(12) United States Patent
Brodsky et al.

(10) Patent No.: US 10,834,491 B2
(45) Date of Patent: Nov. 10, 2020

(54) ELECTRONIC ATTENUATION ADJUSTING HEARING PROTECTION DEVICE

(71) Applicant: INTERNATIONAL BUSINESS MACHINES CORPORATION, Armonk, NY (US)

(72) Inventors: William L. Brodsky, Binghamton, NY (US); Byron S. Green, Poughkeepsie, NY (US); Robert K. Mullady, Ulster, NY (US); Jeffrey A. Newcomer, Poughkeepsie, NY (US); Arkadiy O. Tsfasman, Wappingers Falls, NY (US); John S. Werner, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/145,967

(22) Filed: Sep. 28, 2018

(65) Prior Publication Data

US 2020/0107097 A1    Apr. 2, 2020

(51) Int. Cl.
*H04R 1/10* (2006.01)
*A61F 11/14* (2006.01)
*H04R 5/033* (2006.01)

(52) U.S. Cl.
CPC ........... *H04R 1/1008* (2013.01); *A61F 11/14* (2013.01); *H04R 1/1016* (2013.01); *H04R 1/1041* (2013.01); *H04R 1/1075* (2013.01); *H04R 1/1083* (2013.01); *H04R 5/033* (2013.01); *H04R 2460/11* (2013.01)

(58) Field of Classification Search
CPC .. H04R 1/1008; H04R 1/1041; H04R 1/1083; H04R 5/033; H04R 2201/107; H04R 2460/05; H04R 2460/11; H04R 1/1016; H04R 1/1075; H04R 2460/09; A61F 11/14
USPC ............... 381/71.6, 72, 370, 371, 372, 373; 181/129; 128/867, 868
See application file for complete search history.

(56) References Cited

U.S. PATENT DOCUMENTS

| | | | |
|---|---|---|---|
| 5,332,871 A | 7/1994 | Carrigan | |
| 6,826,287 B2* | 11/2004 | Myers | A61F 11/14 381/370 |
| 9,060,897 B2 | 6/2015 | Marsh | |

(Continued)

FOREIGN PATENT DOCUMENTS

EP    1674059 B1    8/2008

*Primary Examiner* — Huyen D Le
(74) *Attorney, Agent, or Firm* — Cantor Colburn LLP; Teddi Maranzano

(57) ABSTRACT

Acoustic attenuating ear muffs include a first ear pod having a first ear cup provide with a first acoustic attenuating member including an outer surface, and a first opening. A second ear pod includes a second ear cup having a second acoustic attenuating member including an outer surface portion, and a second opening. A first selectively deployable plug member is mounted to the outer surface of the first acoustic attenuating member. A second selectively deployable plug member mounted to the outer surface of the second acoustic attenuating member. An acoustic sensor is operable to detect ambient noise. An actuator system is operable to shift the first and second selectively deployable plug members into corresponding ones of the first and second openings based on ambient noise detected by the acoustic sensor.

14 Claims, 5 Drawing Sheets

(56) References Cited

U.S. PATENT DOCUMENTS

| | | |
|---|---|---|
| 9,333,116 B2 | 5/2016 | Bauman et al. |
| 9,525,929 B2 * | 12/2016 | Burgett ................ H04R 1/1041 |
| 2004/0125976 A1 | 7/2004 | Reneker |
| 2005/0105755 A1 | 5/2005 | Yueh |
| 2012/0305329 A1 | 12/2012 | Keady et al. |
| 2014/0169579 A1 * | 6/2014 | Azmi .................... G10K 11/16 381/71.6 |

* cited by examiner

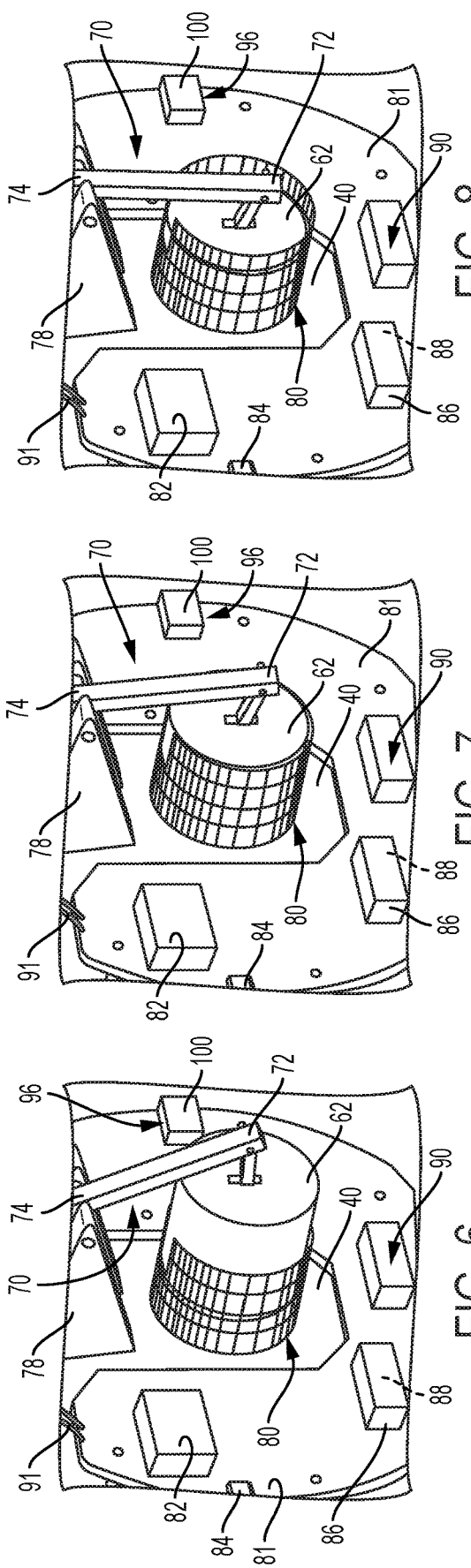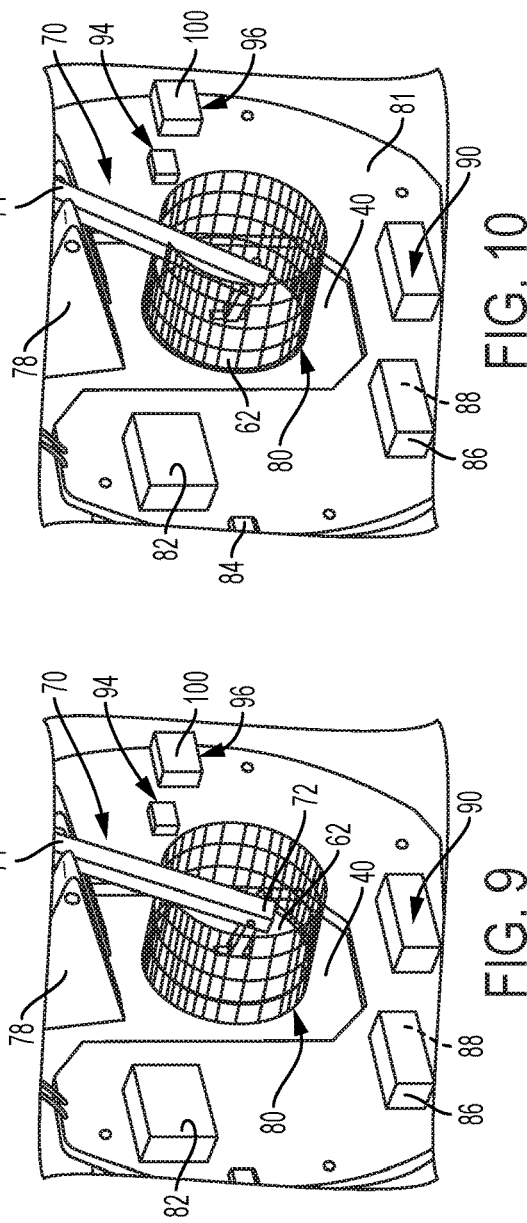

ELECTRONIC ATTENUATION ADJUSTING HEARING PROTECTION DEVICE

BACKGROUND

Exemplary embodiments relate to the art of wearable acoustic attenuation devices and, more particularly, to a wearable acoustic attenuation device including electrically actuated plugs.

Earmuffs that attenuate acoustic noise typically include sound insulating pods that fit over a wearer's ears. The sound insulating pods may include one or more layers of insulation that protect a wearer from sounds over a certain decibel level. In other cases, ear protection may take the form of plugs that fit into an entrance of a wearer's ear canal. While effective, conventional ear muffs and ear protection devices may be awkward, uncomfortable, and present a barrier to communication. Particularly in environments in which ear protection is not a continuous need.

SUMMARY

According to an embodiment of the present invention, acoustic attenuating ear muffs including a first ear pod having a first ear cup provide with a first acoustic attenuating member including an inner surface, an outer surface, and a first opening extending from the outer surface through to the inner surface. A second ear pod includes a second ear cup having a second acoustic attenuating member including an inner surface portion, an outer surface portion, and a second opening extending from the inner surface portion through the outer surface portion. A connecting member links the first ear pod to the second ear pod. A first selectively deployable plug member is mounted to the outer surface of the first acoustic attenuating member. A second selectively deployable plug member mounted to the outer surface of the second acoustic attenuating member. An acoustic sensor is operable to detect ambient noise. An actuator system is operable to shift the first and second selectively deployable plug members into corresponding ones of the first and second openings based on ambient noise detected by the acoustic sensor.

According to another exemplary embodiment, a method of selectively attenuating sound through an acoustic attenuating ear muff includes positioning a first ear pod on a first ear of a wearer and a second ear pod on a second ear of the wearer, detecting a level of ambient noise at the acoustic attenuating ear muff, urging a first selectively deployable plug member into an first opening formed in a first acoustic attenuating member of the first ear pod based on a level of the ambient noise, and urging a second selectively deployable plug member into an second opening formed in a second acoustic attenuating member of the second ear pod based on a level of the ambient noise.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

FIG. 6 depicts an actuator member positioning a selectively deployable plug member in a first attenuation position, in accordance with an aspect of an exemplary embodiment;

FIG. 7 depicts the actuator member positioning the selectively deployable plug member in a second attenuation position, in accordance with an aspect of an exemplary embodiment;

FIG. 8 depicts the actuator member positioning the selectively deployable plug member in a third attenuation position, in accordance with an aspect of an exemplary embodiment;

FIG. 9 depicts the actuator member positioning the selectively deployable plug member in a fourth attenuation position, in accordance with an aspect of an exemplary embodiment;

FIG. 10 depicts the actuator member positioning the selectively deployable plug member in a fifth attenuation position, in accordance with an aspect of an exemplary embodiment.

DETAILED DESCRIPTION

Figure 2:
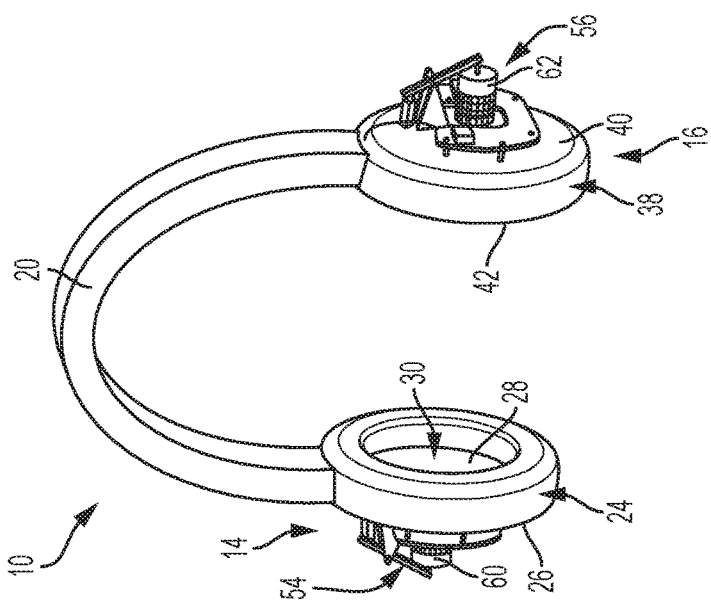
FIG. 2 depicts the acoustic attenuating ear muffs of FIG. 1 with mesh ear covers being removed.
Figure 1:
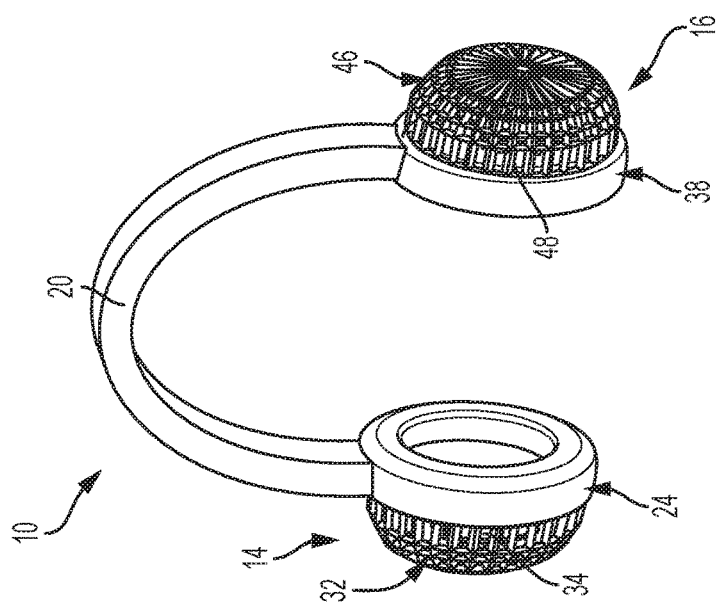
FIG. 1 depicts acoustic attenuating ear muffs, in accordance with an aspect of an exemplary embodiment.

Acoustic attenuating ear muffs, in accordance with an exemplary embodiment, are indicated generally at 10 in FIGS. 1 and 2. Acoustic attenuating earmuffs 10 include a first ear pod 14 coupled to a second ear pod 16 through a connecting member 20. First ear pod 14 includes a first acoustic attenuating member 24 having an outer surface 26 and an inner surface 28. An opening 30 extends from outer surface 26 through to inner surface 28. Opening 30 allows sound to pass through first acoustic attenuating member 24. A first ear cup or cover 32 is mounted to first ear pod 14. First cover 32 includes a plurality of openings 34 that form a mesh (not separately labeled).

Figure 5:
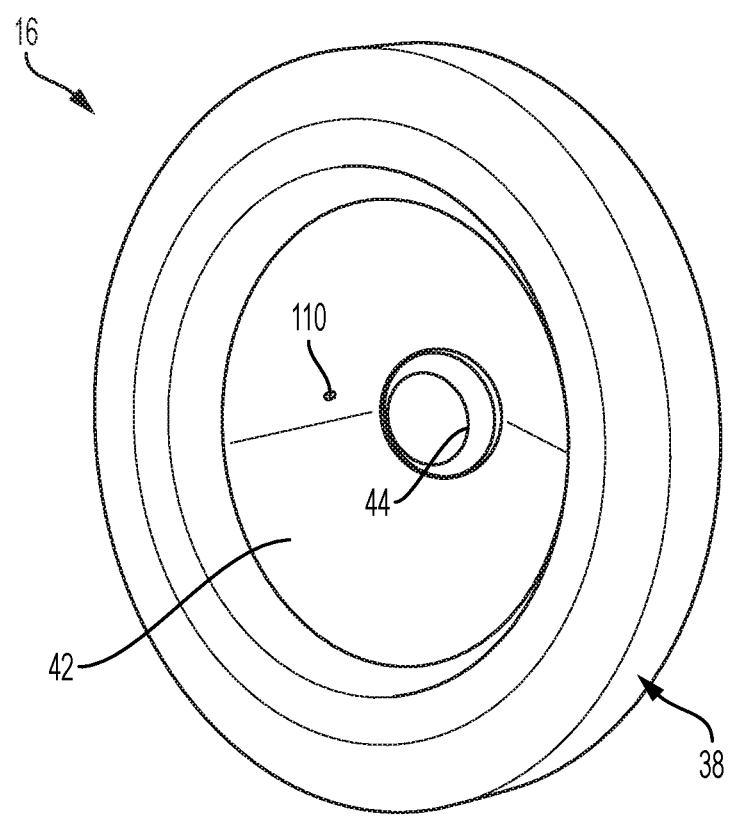
FIG. 5 depicts an inner surface of the ear pod of FIG. 3.

Second ear pod 16 includes a second acoustic attenuating member 38 having an outer surface portion 40 and an inner surface portion 42. An opening 44 (FIG. 5) extends from outer surface portion 40 through to inner surface portion 42. Opening 44 allows sound to pass through second acoustic attenuating member 38. A second ear cup or cover 46 is mounted to second ear pod 16. Second cover 46 includes a plurality of openings, indicated generally at 48, that form a mesh (not separately labeled).

First ear pod 14 supports a first acoustic attenuating system 54 that selectively impedes noise passage through opening 30. Similarly, second ear pod 16 includes a second acoustic attenuating system 56 that selectively impedes noise passage through openings 44. First acoustic attenuating system 54 includes a first selectively deployable plug member 60 and second attenuating system 56 includes a second selectively deployable plug member 62. First and second selectively deployable plug members 60 and 62 are selectively positioned in corresponding ones of opening 30 and opening 44 to impede noise passing through first and second acoustic attenuating members 24 and 38.

Figure 3:
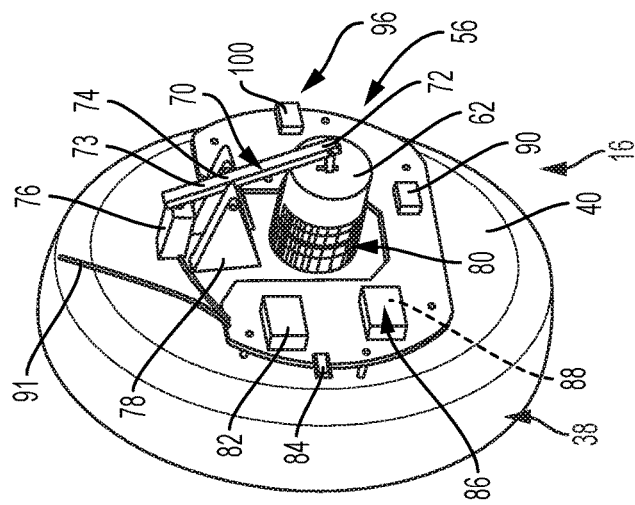
FIG. 3 depicts a left side view of an ear pod of the acoustic attenuating ear muffs of FIG. 1 depicting an actuator member, in accordance with an aspect of an exemplary embodiment.
Figure 4:
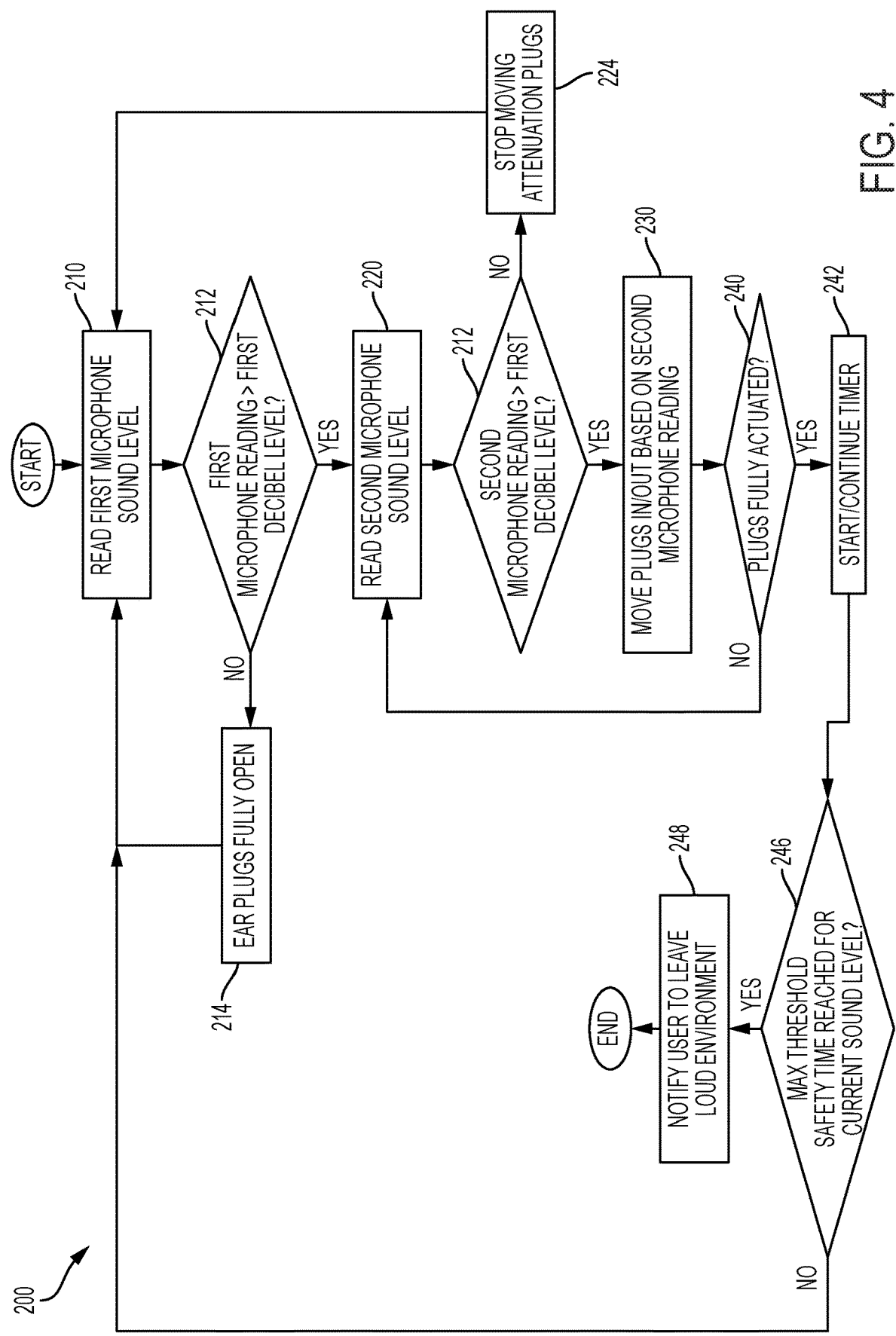
FIG. 4 depicts a right side view of an ear pod of the acoustic attenuating ear muffs of FIG. 1 depicting an actuator member, in accordance with an aspect of an exemplary embodiment.

Reference will now follow to FIGS. 3 and 4, and with continued reference to FIGS. 1 and 2, in describing second acoustic attenuating system 56 with an understanding that first acoustic attenuating system 54 may include similar structure. Second acoustic attenuating system 56 includes a lever 70 having a first end 72, a second end 73, and an intermediate portion 74. First end 72 supports second selectively deployable plug member 62. Second end 73 is connected to an actuator device 76 that selectively pivots lever 70 about a fulcrum 78 mounted to intermediate portion 74. A perforated guide track 80 is mounted to outer surface portion 40 at opening 44. Perforated guide track 80 provides a guide for second selectively deployable plug member 62.

In accordance with an exemplary aspect, second acoustic attenuating system 56 also includes control board 81 that supports a battery 82, a charge port 84, and a controller 86. Charge port 84 may provide a charging connection for both the first and the second attenuating systems 54 and 56. Similarly, battery 82 may provide power to both first and second attenuating systems 54 and 56. Controller 86 includes a processor 88 that may take the form of a central processor unit or CPU. Of course, processor 88 may also take the form of a graphics processing unit or GPU. Processor 88 is coupled to a non-volatile memory 90 through control board 81. Non-volatile memory 90 may have stored thereon a noise value table, an example of which is provided in Table 1 below, which may be factory set or user definable. Table 1 is based on current Occupational Health and Safety Administration (OSHA) guidelines. The noise value table establishes one or more noise thresholds for controlling a position of first selectively deployable plug member 60 and second selectively deployable plug member 62 as will be detailed herein. Controller 86 may be connected to first acoustic attenuating system 54 by a conductor 91 that extends through connecting member 20. Alternative to conductor 91, a wireless transmitter (e.g., Radio Frequency Identification (RFID)) and/or induction coil may be utilized to transfer data and power between first attenuating system 54 and second attenuating system 56.

TABLE 1

| dB Level | When Hearing Damage May Occur |
| --- | --- |
| <85 | No Damage |
| 95 | After 4 Hours of exposure/day |
| 100 | After 2 Hours of exposure/day |
| 105 | After 1 Hours of exposure/day |
| 110 | After 30 Minutes of exposure/day |
| 115 | After 15 Minutes of exposure/day |
| 120 | Almost Immediately |

In an embodiment, second acoustic attenuating system 56 includes a first acoustic sensor 94 mounted to control board 81. A second acoustic sensor 96 may be mounted to control board 81 adjacent to first acoustic sensor 94. First acoustic sensor 94 may take the form of a first microphone 98. Second acoustic sensor 96 may take the form of a second microphone 100. First acoustic sensor 94 may be arranged to detect ambient noise passing through second cover 46. Second acoustic sensor 96 may be arranged to capture noise that has passed through a sound channel 110 shown in FIG. 5 formed in second acoustic attenuating member 38. That is, second acoustic sensor 96 is arranged to detect a noise lever perceived by a wearer of acoustic attenuating earmuffs 10.

In accordance with an exemplary aspect, controller 86 senses, through first acoustic sensor 94, a level of ambient noise at first and second ear pods 14 and 16. If the level of ambient noise is below a predetermined threshold of the noise value table, first and second acoustic attenuating systems 54 and 56 may be operated to shift first and second selectively deployable plug members 60 and 62 to a first attenuation of fully open position, such as shown in FIG. 6. In this position, there is an opening for sound to pass through perforated guide tracks 80 and further through openings 30 and 44 with no blockage by selectively deployable plug members 60 and 62. In this configuration, first acoustic sensors 94 and second acoustic sensors 96 would register substantially similar noise decibel readings.

As the ambient noise increases, first and second acoustic attenuating systems 54 and 56 may be operated to begin to shift first and second selectively deployable plug members 60 and 62 to a second attenuation position such as shown in FIG. 7. The degree of the attenuation may vary from first attenuation position (FIG. 6), to a second attenuation position (FIG. 7), a third attenuation position (FIG. 8), a fourth attenuation position (FIG. 9), and a fifth attenuation position (FIG. 10).

The number of positions may vary and could correspond to the number of rows in the stored noise value table. That is, first and second selectively deployable plug members may be shifted to achieve a desired attenuation that corresponds to a dB level set forth in the stored noise value table. In an alternative embodiment for determining the plug position, first and second selectively deployable plug members 60 and 62 may continue to move until the noise level detected by second acoustic sensor 96 reaches a lower threshold in the noise value table. Further, first and second selectively deployable plug members may be shifted to a greater degree of attenuation after the wearer experiences exposure to noise levels at a particular level for a selected amount of time.

For example, if the current noise level was 105 dB, first and second selectively deployable plug members 60 and 62 could remain in the fully open position for 30 mins because a user will not experience hearing damage at that noise level until 1 hour has passed according to the OSHA limits shown in Table 1. After the first 30 mins, first and second selectively deployable plug members 60 and 62 change position such that the noise exposure on the interior of the ear cup that the user is exposed to is 100 dB. First and second selectively deployable plug members 60 and 62 can remain in this position for a duration of time as long as the total time the user is exposed to noise levels greater than 100 dB is less than 2 hours. First and second selectively deployable plug members 60 and 62 may remain in the second position for 1 hour (which would yield a total time 90 mins that the user is exposed to noise levels greater than or equal to 100 dB). First and second selectively deployable plug members 60 and 62 can be moved to a third position at this point and the method would repeat. This allows the user to better hear within their environment for safety reasons and to communicate with others.

The degree of closure may depend upon a noise level perceived by the wearer. That is, controller 86 may determine a level of noise passing through first and second acoustic attenuating members 24 and 38. For example, controller 86 may, through second acoustic sensor 96 determine a level of noise passing through second acoustic attenuating member 38. A similar sensor (not separately labeled) may be arranged at first acoustic attenuating member 24. Depending upon the level of noise passing through first and second acoustic attenuating members 24 and 38 and the amount of time a wearer is exposed to that particular level, controller 86 may selectively close and/or open first and second openings 30 and 44. The degree of opening may be determined based on acoustic values stored in a noise value table stored in memory 90.

At this point, it should be understood that the exemplary embodiments describe acoustic attenuating ear muffs that may automatically adapt to ambient and/or perceived noise levels to protect a wearer from hearing damage. Adjustments may be made to a degree of attenuation based on changes in ambient noise levels, or an exposure time to noise above one or more set values. For example, after being exposed to noise levels at one level for a first predetermined time period, attenuation may be adjusted to reduce perceived sound levels to provide additional hearing protection even if the ambient noise level does not suggest a need for additional attenuation. By constantly adjusting attenuation to levels that are just below thresholds within a noise value table, the wearer of acoustic attenuation earmuffs 10 will be able to better hear what is going on in their environment both for safety and verbal communication with others.

Figure 11:
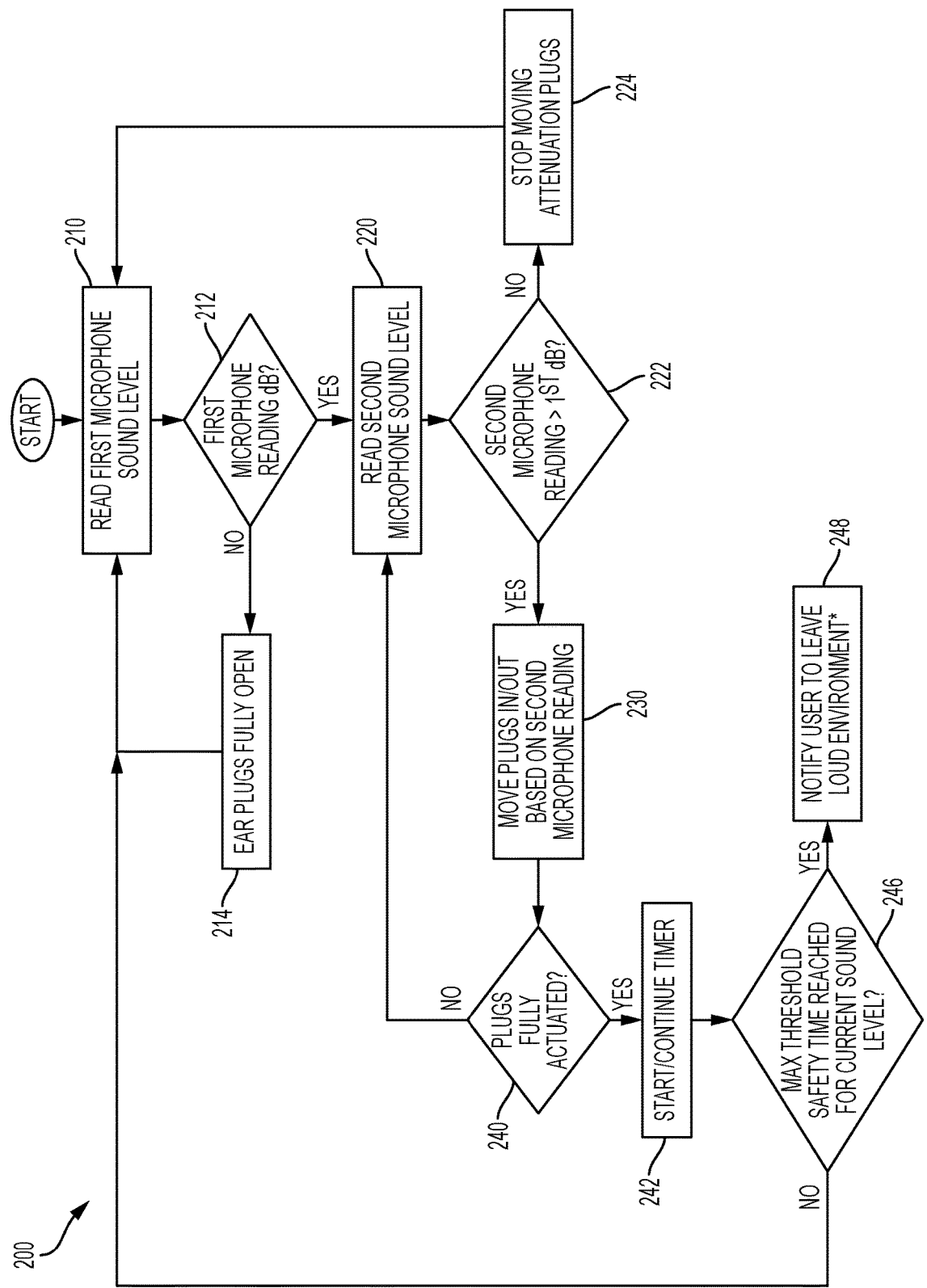
FIG. 11 depicts a flow chart illustrating a method of attenuating noise with the acoustic attenuating ear muffs, in accordance with an aspect of an exemplary embodiment.

Reference will now follow to FIG. 11 in describing a method 200 of attenuating noise with acoustic attenuating ear muffs 10 in accordance with an exemplary embodiment. In block 210 sound at first acoustic sensor 94 is read (e.g., ambient noise level may be read). If, in block 212 the measured sound level is below a first decibel level (e.g., 85 dB when referring to Table 1), first and second selectively deployable plug members 60 and 62 may be positioned fully open in block 214. If the sound level at first acoustic sensor 94 is greater than the first decibel value, sound is read at second acoustic sensor 96 at block 220 (e.g., sound levels on an interior of first and second ear pods 14 and 16). If, in block 222, the sound level detected at second acoustic sensor 96 is below the first decibel level, further movement of first and second selectively deployable plug members 60 and 62 may be stopped as indicated in block 224 (e.g., first and second selectively deployable plug members 60 and 62 do not need to move because they are at a position that creates a safe noise level for the user).

If the sound at second acoustic attenuating member 38 is greater than the first decibel level, first and second selectively deployable plug members 60 and 62 are urged/shifted into first and second openings 30 and 44 as indicated in block 230. In block 240, a determination is made whether first and second selectively deployable plug members 60 and 62 are fully actuated. If, in block 240 it is determined that first and second selectively deployable plug members 60 and 62 are not fully actuated, method 200 returns to block 220. If first and second selectively deployable plug members 60 and 62 are fully actuated, a timer is initiated in block 242. In block 246 a determination is made whether the timer has reached a predetermined time threshold from Table 1 that would indicate unsafe noise levels exposed to the user that could cause temporary and/or permanent hearing loss. If not, method 200 returns to block 210. If the timer has reached the predetermined threshold, a notification is issued in block 248 for the wearer to leave the loud environment. The notification may be an audio signal within the acoustic attenuating ear muffs such as a beep or verbal command or the notification may be provided on a paired device such as a Bluetooth connected mobile device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment of the invention had been described, it will be understood that those skilled in the art, both now and in the future, may make various improvements and enhancements which fall within the scope of the claims which follow. These claims should be construed to maintain the proper protection for the invention first described.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:
1. Acoustic attenuating ear muffs comprising:
  a first ear pod including a first ear cup having a first acoustic attenuating member including an inner surface, an outer surface, and a first opening extending from the outer surface through to the inner surface;
  a first cover mounted over outer surface of the first acoustic attenuating member;
  a second ear pod including a second ear cup having a second acoustic attenuating member including an inner surface portion, an outer surface portion, and a second opening extending from the inner surface portion through the outer surface portion;
  a second cover mounted over the outer surface portion of the second acoustic attenuating member
  a connecting member linking the first ear pod to the second ear pod;
  a first selectively deployable plug member mounted to the outer surface of the first acoustic attenuating member;
  a second selectively deployable plug member mounted to the outer surface of the second acoustic attenuating member;
  an acoustic sensor operable to detect ambient noise; and
  an actuator system operable to shift the first and second selectively deployable plug members into correspond- ing ones of the first and second openings based on ambient noise detected by the acoustic sensor.

2. The acoustic attenuating ear muffs according to claim 1, wherein the acoustic sensor is arranged on at least one of the outer surface of the first ear cup and the outer surface portion of the second ear cup.

3. The acoustic attenuating ear muffs according to claim 2, further comprising: another acoustic sensor operable to detect noise between the inner surface and a wearer's ear in at least one of the first ear cup and the second ear cup.

4. The acoustic attenuating ear muffs according to claim 3, wherein the another acoustic sensor is arranged on one of the outer surface of the first ear cup and the outer surface portion of the second ear cup.

5. The acoustic attenuating ear muffs according to 4, further comprising: a sound channel extending through the one of the first ear cup and the second ear cup, the sound channel connecting the corresponding one of the inner surface and the inner surface portion with the another acoustic sensor.

6. The acoustic attenuating ear muffs according to claim 1, wherein the actuator system includes a first actuator device coupled to the first selectively deployable plug member and a second actuator device coupled to the second selectively deployable plug member.

7. The acoustic attenuating ear muffs according to claim 6, further comprising: a first guide track mounted to the outer surface and a second guide track mounted to the outer surface portion, the first guide track guiding the first selectively deployable plug member into the first opening and the second guide track guiding the second selectively deployable plug member into the second opening.

8. The acoustic attenuating ear muffs according to claim 7, wherein the first actuator device includes a first lever that selectively shifts the first selectively deployable plug member along the first guide track into the first opening and the second actuator device includes a second lever that selectively shifts the second selectively deployable plug member along the second guide track into the second opening.

9. A method of selectively attenuating sound through an acoustic attenuating ear muff comprising:
positioning a first ear pod having a first acoustic attenuating member and a first cover on a first ear of a wearer and a second ear pod having a second acoustic attenuating member and a second cover on a second ear of the wearer;
detecting a level of ambient noise at the acoustic attenuating ear muff;
activating a first actuator to pivot a first lever coupled to a first selectively deployable plug member about a first fulcrum into a first opening formed in the first acoustic attenuating member of the first ear pod based on a level of the ambient noise; and
activating a second actuator to pivot a second lever coupled to a second selectively deployable plug member about a second fulcrum into a second opening formed in the second acoustic attenuating member of the second ear pod based on a level of the ambient noise.

10. The method of claim 9, further comprising:
detecting an amount of noise passing into the first ear pod and the second ear pod; and
adjusting a position of the first and second selectively deployable plug members based on the amount of noise passing into the first ear pod and the second ear pod.

11. The method of claim 9, wherein activating the first and second actuators to shift the first and second selectively deployable plug members into corresponding first and second openings based on the level of the ambient noise comprises comparting the amount of ambient noise to a noise value table.

12. The method of claim 11, further comprising: establishing an amount of noise attenuation based on the noise value table.

13. The method of claim 9, wherein activating the first and second actuators to shift the first and second selectively deployable plug members into corresponding first and second openings includes shifting the first and second selectively deployable plug members along corresponding first and second guide tracks.

14. The method of claim 9, wherein activating the first and second actuators includes pivoting the a first lever about the first fulcrum attached to an outer surface of the first ear pod and pivoting the a second lever about the second fulcrum attached to an outer surface portion of the second ear pod.

* * * * *